United States Patent [19]
Grasselli et al.

[11] 3,978,003
[45] *Aug. 31, 1976

[54] PROCESS FOR THE OXIDATION OF OLEFINS TO UNSATURATED ALDEHYDES AND NITRILES AND CATALYSTS THEREFORE

[75] Inventors: Robert K. Grasselli, Warrensville Hts.; Maria S. Friederich, Cleveland, both of Ohio

[73] Assignee: Standard Oil Company, Cleveland, Ohio

[ * ] Notice: The portion of the term of this patent subsequent to June 17, 1992, has been disclaimed.

[22] Filed: Jan. 22, 1974

[21] Appl. No.: 435,447

Related U.S. Application Data

[60] Division of Ser. No. 205,705, Dec. 7, 1971, Pat. No. 3,859,358, and a continuation-in-part of Ser. No. 16,923, March 5, 1970, Pat. No. 3,666,822, which is a continuation of Ser. No. 691,934, Dec. 20, 1967, Pat. No. 3,542,842.

[52] U.S. Cl. .................... 252/456; 252/458; 252/467; 252/469; 252/470; 260/465.3; 260/604 R

[51] Int. Cl.² .................... B01J 23/28; B01J 23/88
[58] Field of Search .......... 252/456, 458, 467, 469, 252/470

[56] References Cited
UNITED STATES PATENTS
3,471,545   10/1969   Giordano et al. .................. 252/458

*Primary Examiner*—W. J. Shine
*Attorney, Agent, or Firm*—Herbert D. Knudsen; Larry W. Evans; Evelyn R. Kosman

[57] ABSTRACT

Catalysts are provided which are useful in the oxidation of olefins to aldehydes and conjugated dienes and in ammoxidation of olefins to nitriles. The catalysts comprise the combined oxides of uranium and molybdenum and the combined oxides of uranium and molybdenum in combination with arsenic, bismuth, tin, vanadium, iron, nickel and cobalt.

6 Claims, No Drawings

PROCESS FOR THE OXIDATION OF OLEFINS TO UNSATURATED ALDEHYDES AND NITRILES AND CATALYSTS THEREFORE

CROSS-REFERENCE TO RELATED APPLICATIONS

This is a divisional of application Ser. No. 205,705 filed Dec. 7, 1971, now U.S. Pat. No. 3,859,358 issued Jan. 1, 1975. This application is a continuation-in-part of our U.S. Patent application Ser. No. 16,923 filed Mar. 5, 1970, now U.S. Pat. No. 3,666,822, issued May 30, 1972, which is a continuation of U.S. Patent application Ser. No. 691,934 filed Dec. 20, 1967, now U.S. Pat. No. 3,542,842.

This invention relates to oxidation catalysts comprising oxides of uranium and molybdenum optionally incorporating promoters, which are useful for the catalytic oxidation of olefins to unsaturated aldehydes and acids, conjugated dienes, and for the catalytic ammoxidation of olefins to unsaturated nitriles. The catalytic oxidation reactions are exemplified by the oxidation of propylene to acrolein and acrylic acid, the oxidation of isobutylene to methacrolein, the oxydehydrogenation of an olefin having four to eight carbons, such as the oxydehydrogenation of butene-1 or butene-2 to butadiene-1,3, the ammoxidation of propylene to acrylonitrile and the ammoxidation of isobutylene to methacrylonitrile.

The prior art is replete with a multiplicity of oxidation catalysts particularly suited to the same reactions disclosed herein. Some of these oxidation catalysts are disclosed in U.S. Pat. Nos. 2,904,580; 3,142,697; 3,179,694; 3,197,419; 3,198,750; 3,200,081; 3,200,084; 3,226,421; 3,248,340; 3,264,225; 3,251,900; 3,257,474; 3,260,768; French Pat. Nos. 1,255,121; 1,269,382; and British Pat. Nos. 864,666; 876,446; 983,755. It is well known that some catalysts make for more successful processes than others and that the search for economically competitive superior catalysts continues unremittingly. The oxidation catalyst of the instant invention is such a catalyst.

DESCRIPTION OF PREFERRED EMBODIMENT OF THE INVENTION

The uranium oxide-molybdenum oxide base catalyst disclosed herein is referred to as a mixture of uranium and molybdenum oxides, but this is not to be construed as meaning that the catalyst is composed either in whole or in part of only these compounds. The proportions of uranium and molybdenum in the catalyst system may vary widely. The preferred uranium:molybdenum atomic ratio ranges from about 1:25 to about 25:1; optimum activity appears to be obtained at uranium:molybdenum atomic ratios within the range of from about 1:1 to about 1:6 and the catalyst is characterized by a negligible loss of activity and selectivity over extended periods of time despite the relatively high reaction temperatures of the catalytic processes in which it is useful.

Though the unsupported catalyst of the instant invention gives good results, a preferred catalyst contains from 5 percent to 95 percent by weight of a catalyst support, and preferably between 10 percent and 90 percent. Any known catalyst support such as alumina, pumice, silicon carbide, zirconia, titania, alumina-silica, and the inorganic phosphates, silicates, aluminates, borates and carbonates stable under the reaction conditions, may be used but silica is preferred.

In the preparation of the base catalyst useful in this invention, the molybdenum oxide and uranium oxide can be blended together or can be formed separately and then blended, or formed separately, or together in situ.

The uranium oxide component of the instant catalyst can be useful in the form of uranous, uranic, or combined uranous-uranic oxides, or by precipitation in situ from a soluble uranyl salt, such as the nitrate, acetate or a halide such as the chloride. The preferred manner of arriving at the oxides of the instant catalyst is by use of the water-soluble salts of uranium and molybdenum. Uranium metal can be used as a starting material, and if molybdenum metal is also employed the molybdenum can be converted to the oxide and the uranium to the nitrate simultaneously by oxidation in hot nitric acid. A slurry of hydrous molybdenum-molybdenum oxide in nitric acid can be combined with a solution of a uranium salt and the hydroxides co-precipitated in situ by making the solution alkaline with ammonium hydroxide. If desired, the ammonium salts formed may be removed by filtration, thermal decomposition, or any other means. Generally, it will suffice to evaporate the precipitated hydroxides to dryness without filtration.

It will be apparent from the above that uranous and uranic bromides, chlorides, fluorides and iodides, nitrates, acetates, sulfites, sulfates, phosphates, thiocyanates, thiosulfates, oxalates, formates and hydroxides can be employed as the source of the uranium oxide components. A preferred source is uranyl nitrate.

As starting materials for the molybdenum oxide component, there can be used any molybdenum oxide such as the dioxide, trioxide, pentoxide or sesquioxide; or a hydrolyzable or decomposable molybdenum salt such as a molybdenum halide. Molybdenum metal can be employed, the oxide being formed by oxidizing the metal with an oxidizing acid, such as nitric acid. A preferred starting material is ammonium heptamolybdate.

Other variations in starting materials will suggest themselves to one skilled in the art, particularly when the preferred starting materials mentioned hereinabove are unsuited to the economics of large-scale manufacture. In general, any uranium and molybdenum containing components may be used provided that they result, upon heating to a temperature within the range disclosed hereinafter, in the oxides of the instant catalyst.

The catalytic activity of the novel catalyst embodied in the present invention is enhanced by heating the catalyst at an elevated temperature. Preferably, the catalyst mixture is dried and heated at a temperature of from 500°F to 1100°F more preferably at about 600°F to 800°F for from 2 to 24 hours. If activity is insufficient, the catalyst can be further heat-treated at a temperature above about 800°F but below a temperature deleterious to the catalyst at which it is melted or decomposed, preferably in the range from about 800°F to about 1400°F for from 1 to 48 hours, in the presence of oxygen or an oxygen-containing gas such as air.

There appears to be no readily discernible correlation between activation temperature and the time required to effect activation. The sufficiency of activation at any given set of conditions is ascertained by a spot test of a sample of the material for catalytic activity. Activation is best carried out in an open chamber, permitting circulation of air or oxygen, so that any oxygen consumed will be replaced.

It has also been found that some of the instant catalysts can be further activated by subjecting heat-treated catalyst to a reducing atmosphere for a period of from about 4 to about 48 hours at a temperature in the range from about 400°F to about 1000°F. This reducing treatment is conveniently accomplished by flowing a reducing gas such as ammonia, hydrogen or the like over the catalyst. It was found that catalysts treated with a reducing gas gave higher conversions after a short period of time during which the conversions were actually lower than those given by the same catalysts without the reducing treatment.

The instant catalyst comprising the combined oxides of uranium and molybdenum may be defined by the following empirical formula $U_x Mo_y O_z$ where $x$ is a number within the range from 1 to about 25, $y$ is a number of from 1 to about 25, and $z$ is determined by the oxidation state of U and Mo in the catalyst. It is conjectured that at least some of the combined oxides of the instant catalyst are present as an activated catalytic oxide complex.

Various metal oxides have been found to act as promoters in conjunction with the uranium-molybdenum oxides base catalyst, as for example, elements selected from Groups I-A, I-B, II-A, II-B, III-B, IV-A, IV-B, V-B, VI-B, VII-B, and VIII of the Periodic Table. (See *Handbook of Chemistry*, 38th Edition, Chemical Rubber Publishing Co., Periodic Chart of the Elements, pg. 394 and 395.) Particularly effective promoters are the oxides of arsenic, bismuth, tin, vanadium, iron, nickel, and cobalt, in an amount in the range corresponding to from about 0.001 to 3 atomic equivalent per atomic equivalent of either uranium or molybdenum. These catalysts are designated by the empirical formula $M_a U_x Mo_y O_z$ where M denotes at least one promoter element; $a$ is a number within the range of 0.001 up to about 3; $x$ is a number within the range of from 1 to about 25; and $y$ is a number of from 1 to about 25; and $z$ is a number taken to satisfy the average valences of uranium, molybdenum and the promoter element in the oxidation states in which they exist in the catalyst.

Promoter oxides may be incorporated into the base catalyst by blending into the gel before calcining, or by blending into the oven-dried base catalyst before calcining. A preferred manner of incorporating promoter elements is by chossing a water-soluble salt of the promoter element, forming an aqueous solution of the salt, and mixing this solution with uranyl nitrate and ammonium heptamolybdate solutions, and stirring while continuously heating till the solution gels. The gel is then spooned into trays and oven-dried at 120°C overnight. The dried catalyst is calcined starting at 500°F; the temperature was raised to 800°F over a period of two hours and the catalyst was calcined overnight at this temperature. A further calcination at a higher temperature of 900°F for three hours sometimes was given to increase the activity of the catalyst complex. This catalyst system is useful in the oxidation of olefins to oxygenated compounds, such as aldehydes and acids, in the presence of oxygen; in the oxidation of olefins to unsaturated nitriles in the presence of oxygen and ammonia; and in the oxydehydrogenation of olefins to diolefins and aromatic compounds. Nitriles and oxygenated compounds such as aldehydes and acids can be produced simultaneously using process conditions within the overlapping ranges for these reactions as set forth in detail below. The relative proportions of each that are obtainable will depend on the process conditions, the particular catalyst and on the olefin. The term "oxidation" as used in this specification and claims encompasses the oxidation to aldehydes and acids and to nitriles and dienes all of which conversions require oxygen as a reactant.

OXIDATION OF OLEFINS TO OXYGENATED COMPOUNDS

The reactants used in the oxidation to oxygenated compounds are oxygen and an olefin having only three carbon atoms in a straight chain such as propylene or isobutylene or mixtures thereof.

The olefins may be in admixture with paraffinic hydrocarbons, such as ethane, propane, butane and pentane; for example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e., −10 to 100 psig, temperatures in the range of 500°F to 1100°F may be advantageously employed. However, the process may be conducted at other pressures, and in the case where superatmospheric pressures, e.g., above 100 psig, are employed, somewhat lower temperatures are possible. In the case where this process is employed to convert propylene to acrolein, a temperature range of 750°F to 950°F has been found to be optimum at atmospheric pressure.

While pressures other than atmospheric may be employed, it is generally preferred to operate at or near atmospheric pressure, since the reaction proceeds well at such pressures and the use of expensive high pressure equipment is avoided.

The apparent contact time employed in the process is not critical and it may be selected from a broad operable range which may vary from 0.1 to 50 seconds. The apparent contact time may be defined as the length of time in seconds which the unit volume of gas measured under the conditions of reaction is in contact with the apparent unit volume of the catalyst. It may be calculated, for example, from the apparent volume of the catalyst bed, the average temperature and pressure of the reactor, and the flow rates of the several components of the reaction mixture.

The optimum contact time will, of course, vary depending upon the olefin being treated, but in the case of propylene and isobutylene, the preferred apparent contact time is 0.15 to 15 seconds.

A molar ratio of oxygen to olefin between about 0.5:1 to 5:1 generally gives the most satisfactory results. For the conversion of propylene to acrolein, a preferred ratio of oxygen to olefin is from about 1:1 to about 2:1. The oxygen used in the process may be derived from any source; however, air is the last expensive source of oxygen and is preferred for that reason.

Water is formed as a product of reaction and it has been found that it has a beneficial influence on the course of the reaction in that it improves the conversion and the yields of the desired product. Sometimes it is desirable to add some water to the reaction mixture. The manner in which water affects the reaction is not fully understood but the theory of this phenomenon is not deemed important in view of the experimental results we have obtained.

OXIDATION OF OLEFINS TO NITRILES

The reactants are the same as those used in the oxidation of olefins to aldehydes described above except that ammonia is included as a reactant. Any of the olefins described above can be used.

In its preferred aspect, the process comprises contacting a mixture comprising propylene or isobutylene, ammonia and oxygen with either the promoted or unpromoted catalyst of this invention at an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give equivalent results. The molar ratio of oxygen to the olefin in the feed to the reaction vessel should be in the range of 0.5:1 to 4:1 and a ratio of about 1:1 to 3:1 is preferred.

Low molecular weight saturated hydrocarbons do not appear to influence the reaction to an appreciable degree, and these materials can be present; consequently the addition of saturated hydrocarbons to the feed to the reaction is contemplated within the scope of this invention. Likewise, diluents, such as nitrogen and the oxides of carbon, may be present in the reaction mixture without deleterious effect.

The molar ratio of ammonia to olefin in the feed to the reactor may vary between about 0.05:1 to 5:1. There is no real upper limit for the ammonia:olefin ratio, but there is generally no reason to exceed the 5:1 ratio. At ammonia:olefin ratios appreciably less than the stoichiometric ratio of 1:1, various amounts of oxygenated derivatives of the olefin will be formed.

Significant amounts of unsaturated aldehydes, as well as nitriles, will be obtained at ammonia:olefin ratios substantially below 1:1, i.e., in the range of 0.15:1 to 0.75:1. Outside the upper limit of this range only insignificant amounts of aldehydes will be produced, and only very small amounts of nitriles will be produced at ammonia:olefin ratios below the lower limit of this range. It is fortuitous that within the ammonia:olefin range stated, maximum utilization of ammonia is obtained and this is highly desirable. It is generally possible to recycle any unreacted olefin and unconverted ammonia.

A particularly surprising aspect of this invention is the effect of water on the course of the reaction. We have found that in many cases water in the mixture fed to the reaction vessel improves the selectivity of the reaction and the yield of nitrile. However, reactions not including water in the feed are not to be excluded from this invention inasmuch as water is formed in the course of the reaction.

In general, the molar ratio of added water to olefin, when water is added, is at least about 0.25:1. Ratios on the order of 1:1 to 3:1 are particularly desirable, but higher ratios may be employed, i.e., up to about 10:1.

The reaction is carried out at a temperature within the range of from about 550°F to 1100°F. The preferred temperature range is from about 800°F to 1000°F.

The pressure at which the reaction is conducted is also an important variable, and the reaction should be carried out at about atmospheric or slightly above atmospheric (2 to 3 atmospheres) pressure. In general, high pressures, i.e., about 250 psig, are not suitable, since higher pressures tend to favor the formation of undesirable by-products.

The apparent contact time is not critical, and contact times in the range of from 0.1 to about 50 seconds may be employed. The optimum contact time will, of course, vary depending upon the olefin being treated, but in general, a contact time of from 1 to 15 seconds is preferred.

THE OXIDATIVE DEHYDROGENATION OF OLEFINS TO DIOLEFINS AND AROMATICS

In accordance with the present invention, the promoted or unpromoted catalyst system is employed in the catalytic oxidative dehydrogenation of olefins to diolefins and aromatic compounds. In the process, the feed stream in vapor form containing the olefin to be dehydrogenated and oxygen is conducted over the promoted catalyst at a comparatively low temperature to obtain the corresponding diolefin or aromatic compound.

By the term "olefin" as used herein is meant the open chain as well as cyclic olefins. The olefins dehydrogenated in accordance with this invention have at least four and up to about eight non-quaternary carbon atoms, of which at least four are arranged in series in a straight chain or ring. The olefin preferably are either normal straight chain or tertiary olefins. Both cis- and trans-isomers, where they exist, can be dehydrogenated.

Among the many olefinic compounds which can be dehydrogenated in this way are butene-1; butene-2; pentene-1; pentene-2; heptene-1; octene-1; tertiary pentenes and hexenes having one tertiary carbon atom such as 2-methyl-pentene-1, 3-methylbutene-1, 3,4-dimethyl-pentene-1, 4-methyl-pentene-2, other branched chain olefins such as 2-methyl-butene-2, 2-methyl-butene-1, 3-methyl-pentene-2; cyclo-olefins such as cyclopentene; cyclohexene; 3-methyl cyclohexene and cycloheptene.

Open chain olefins yield diolefins, and, in general, six-membered ring olefins yield aromatic ring compounds. The higher molecular weight open chain olefins may cyclize to aromatic ring compounds.

The feed stock in addition to the olefin and oxygen can contain one or more paraffinic or naphthenic hydrocarbons having up to about 10 carbon atoms, which may be present as impurities in some petroleum hydrocarbon stocks and which may also be dehydrogenated in some cases. In this oxidative dehydrogenation reaction, propylene and isobutylene should not be included in the feed in substantial amounts.

The amount of oxygen should be within the range of from about 0.3 to about 3 moles per mole of olefin. Stoichiometrically 0.5 to 1.5 moles of oxygen per mole of olefin is required for the dehydrogenation to diolefins and aromatics, respectively. It is preferred to employ an excess of oxygen, from 1 to about 2 moles per mole of olefin, in order to ensure a higher yield of diolefin per pass. The oxygen can be supplied as pure or substantially pure oxygen or as air or in the form of hydrogen peroxide.

When pure oxygen is used, it may be desirable to incorporate a diluent in the mixture such as steam, carbon dioxide or nitrogen.

The feed stock is preferably catalytically dehydrogenated in the presence of steam, but this is not essential. Usually, from about 0.1 to about 6 moles of steam per mole of olefin reactant is employed, but amounts larger than this can be used.

The dehydrogenation proceeds at temperatures within the range of from about 325°C to about 1000°C. Optimum yields are obtainable at temperatures within the range from about 400°C to 550°C. However, since the reaction is exothermic, temperatures in excess of 550°C should not be used, unless means are provided to carry off the heat liberated in the course of the reaction. Due to the exothermic nature of the reaction, the temperature of the gaseous reaction mixture will be higher than the temperature of the feed entering the system by as much as 75°C. The temperatures referred to are those of the entering gas feed near the reactor inlet.

The preferred reaction pressure is approximately atmospheric, within the range of from about 5 to about 75 psig. Higher pressures up to about 300 psig can be used and have the advantage of simplifying the product recovery.

Only a brief contact time with the catalyst is required for effective dehydrogenation. The apparent contact time with the catalyst can vary from about 0.5 up to about 50 seconds but higher contact times can be used if desired. At these contact times, comparatively small reactors and small amounts of catalyst can be used effectively.

In general, any apparatus of the type suitable for carrying out oxidative reactions in the vapor phase may be employed in the execution of these processes. The processes may be conducted either continuously or intermittently. The catalyst bed may be a fixed bed employing a large particulate or pelleted catalyst or, in the alternative, a so-called "fluidized" bed of catalyst may be employed.

The reactor may be brought to the reaction temperature before or after the introduction of the reaction feed mixture. However, in a large-scale operation, it is preferred to carry out the process in a continuous manner, and in such a system, the recirculation of the unreacted olefin is contemplated.

The catalyst compositions and oxidation process of this invention are further illustrated in the following examples wherein the amounts of the various ingredients are expressed as parts by weight unless otherwise specified.

EXAMPLE 1

In a typical preparation of the unpromoted catalyst, 53.2 parts of ammonium molybdate $(NH_4)_6 Mo_7O_{24}.4H_2O$ were dissolved in 100 parts of water; 50.2 parts of uranyl nitrate $(UO_2)(NO_3)_2.6H_2O$ were dissolved in 100 parts of water. These two solutions were added to 49.0 parts Ludox AS, a 30 percent by weight dispersion of silica in water. The resulting mixture was heated on a hot plate with constant stirring until it gelled. The gel was spooned into trays, placed in an atmospheric convection oven at about 120°C and dried for about 24 hours. The oven-dried catalyst was then heat-treated in a furnace open to the atmosphere at 800°F for 21.5 hours. The catalyst obtained had a composition which may be written as 82.5% $Mo_3U_1O_x$ — 17.5% $SiO_2$, where $x$ is a number chosen to satisfy the oxidation states of molybdenum and uranium as they exist in the heat-treated catalyst complex. In this preparation $x$ is thought to be about 10.5.

EXAMPLE 2

A portion of the above-described catalyst (calcined at 800°F) was further calcined at 1050°F for three hours.

EXAMPLE 3

A catalyst system containing iron and bismuth as promoters was prepared as follows: 48.4 g. of $Fe(NO_3)_3.9H_2O$ were dissolved in 100 ml. water and 9.7 g. of $Bi(NO_3)_3.5H_2O$ were dissolved in 50 ml. of a 10% $HNO_3$ acid solution. 60.3 g. $UO_2(NO_3)_2.6H_2O$ and 42.4 g. $(NH_4)_6 Mo_7O_{24}.4H_2O$ were dissolved in about 500 ml. water and the ferric nitrate and bismuth nitrate solutions added. 59.0 g. of Ludox AS were added to the total and the mixture stirred thoroughly while being heated, until it thickened. It was then dried in a drying oven at about 130°C overnight. The dried catalyst was then heat-treated in a furnace open to the atmosphere at 800°F for 16 hours and further heat-treated at 1050°F–1100°F for three hours. The composition of the promoted catalyst formed may be written 82.5% $Fe_6U_6Bi_1Mo_{12}O_x$ — 17.5% $SiO_2$ and $x$ is thought to be about 65.5.

EXAMPLE 4

A catalyst system containing arsenic as promoter was prepared as follows: 53.2 g. $(NH_4)_6 Mo_7O_{24}.4H_2O$ were dissolved in about 100 ml. water; 150.6 g. $UO_2(NO_3)_2.6H_2O$ were dissolved in about 200 ml. water; 3.8 g. $H_3AsO_4.\frac{1}{2} H_2O$ were dissolved in about 50 ml. water.

The solutions were mixed and 91.2 g. Ludox AS, a 30% by weight silica dispersion in water, was added to the mixture. The mixture was heated until it thickened; it was then spooned into a dish and oven-dried at about 130°C overnight. The dried catalyst was heat-treated in a furnace open to the atmosphere at 800°F overnight.

EXAMPLE 5

A catalyst system containing iron as promoter was prepared as follows: 150.6 g. $UO_2(NO_3)_2.6H_2O$ were dissolved in about 200 ml. of water; 53.2 g. $(NH_4)_6Mo_7O_{24}.4H_2O$ were dissolved in about 100 ml. of water; 10.1 g. $Fe(NO_3)_3.9H_2O$ were dissolved in about 50 ml. of water.

The solutions were mixed and 93.0 g. Ludox AS, a dispersion of 30% by weight silica in water, was added to the solution. The mixture was heated with constant stirring until it started to gel. The thickened mixture was then spooned into a dish and oven-dried at 130°C overnight. The dried catalyst was heat-treated at 800°F for 64 hours in a furnace open to the atmosphere.

EXAMPLE 6

A catalyst system containing bismuth as promoter was prepared as follows: 53.2 g. $(NH_4)_6Mo_7O_{24}.4H_2O$ were dissolved in about 100 ml. of water; 150.6 g. $UO_2(NO_3)_2.6H_2O$ were dissolved in about 200 ml. of water; 12.1 g. $Bi(NO_3)_3.5H_2O$ were dissolved in about 50 ml. of a 10% $NHO_3$ acid solution. The solution were mixed and 95.6 g. Ludox AS, a dispersion of 30% silica by weight in water, was added to the solution. The mixture was heated with constant stirring until it started to gel. The thickened mixture was then spooned into a dish and oven-dried at 130°C overnight. The dried catalyst was heat-treated at 800°F overnight. The composition of the promoted catalyst formed may be written 82.5% $Mo_3U_3Bi_{0.25}O_x$ — 17.5% $SiO_2$ and $x$ is thought to be about 18.6.

Other promoted catalyst systems were prepared in a manner similar to that described in the example hereinabove, utilizing the soluble salts of the promoter desired to be incorporated. In general, it is preferred to use the nitrates of the promoter elements though other salts may be used. The amount of soluble salt used is determined by the concentration of the promoter desired in the catalyst. The amount of Ludox solution used is determined by the proportion of 'active' material to catalyst support desired.

Using the procedure outlined above, various embodiments of the promoted catalysts disclosed herein were prepared and tested.

EXAMPLES 7–13

A catalyst system composed of molybdenum oxide and uranium oxide having a Mo:U atomic ratio of 3:1 was prepared as described in Example 1 and was used for the oxidation of propylene to acrylonitrile. A fixed bed microreactor was employed in the form of a 5/16-inch diameter tube 5½ inches long, into which was charged about 7 g. of catalyst. The gas feed (propylene, ammonia, and air) was metered by Rotameters. The table below lists silica supported catalyst systems having other Mo:U ratios (in addition to that having a Mo:U atomic ratio of 3:1), prepared in a manner similar to that described in Example 1 except that different quantities of ingredients were used, and gives reactor temperatures for runs made at substantially atmospheric pressure with a feed molar ratio of Propylene-/Ammonia/Air = 1/1.1/12 and an apparent contact time of about 3 seconds. The apparent contact time is defined as the length of time in seconds which the unit volume of gas measured under reaction conditions is in contact with the apparent unit volume of catalyst. Heat treatment temperatures for catalyst in the Table I refer to heat in addition to that given the catalyst as described in Example 1.

TABLE I

| Ex. No. | Atomic Ratio Mo:U | Heat-Treated Catalyst Temp. °F | Time, Hrs. | Reactor Temp. °F | Percent Conversion per Pass Acrylonitrile | Acrolein | HCN |
|---|---|---|---|---|---|---|---|
| 7 | 3 | 800 | 24 | 830 | 45.3 | 5.2 | 3.9 |
| 8 | 3 | 1000 | 3 | 845 | 41.8 | 10.9 | 1.9 |
| 9 | 2 | 1075 | 3 | 860 | 16.7 | 8.0 | 5.6 |
| 10 | 1 | 1075 | 3 | 810 | 10.2 | Trace | 9.9 |
| 11 | 0.5 | 1075 | 3 | 790 | 5.0 | Trace | 6.9 |
| 12 | 4.6 | 1075 | 3 | 860 | 19.7 | Trace | 5.2 |
| 13 | 9.2 | 1075 | 3 | 925 | 10.4 | 8.9 | 3.3 |

EXAMPLES 14–15

A catalyst system composed of molybdenum oxide and uranium oxide having a Mo:U atomic ratio of 3:1 was prepared as described in Example 2, and was used for the oxidation of propylene to acrolein. A fixed bed microreactor was employed in the form of a 5/16-inch diameter tube, 5½ inches long, into which was charged about 7 g. of catalyst. The gas feed (propylene and air) was metered by Rotameters. The Table II below lists silica supported catalyst systems having other Mo:U ratios (in addition to that having a Mo:U atomic ratio of 3:1) and gives reactor temperatures for runs made at substantially atmospheric pressure with a feed molar ratio of Propylene/Air = 1/12 and an apparent contact time of about three seconds. Heat-treated catalyst temperatures in Table II refer to heat-treatment in addition to that given the catalyst as described in Example 1.

TABLE II

| Ex. No. | Atomic Ratio Mo:U | Heat-Treated Catalyst Temp. °F | Time, Hrs. | Reactor Temp. °F | Percent Conversion per Pass Acrolein | Acrylic Acid |
|---|---|---|---|---|---|---|
| 14 | 3/1 | 1075 | 3 | 770 | 41.3 | 5.7 |
| 15 | 12/1 | 1075 | 3 | 820 | 48.5 | 7.2 |

EXAMPLES 16–18

A catalyst system composed of molybdenum oxide and uranium oxide having a Mo:U atomic ratio of 3:1 was prepared as described in Example 1, and was used for the oxydehydrogenation of butylenes to butadiene. A fixed bed microreactor was employed in the form of a 5/16-inch diameter tube, 5½ inches long, into which was charged about 7 g. of catalyst. The gas feed in the Examples below consisted of substantially pure 1-butene and air which was metered by Rotameters. Mixtures of butenes, or predominantly 2-butene, may also be used. The Table III below lists silica supported catalyst systems having other Mo:U ratios (in addition to that having a Mo:U atomic ratio of 3:1) and gives reactor temperatures for runs made at substantially atmospheric pressure with a feed molar ratio of Butylene-/Air = 1/12 and an apparent contact time of about 3 seconds. Heat-treated catalyst temperatures in Table III refer to heat-treatment in addition to that given the catalyst as described in Example 1.

TABLE III

| Ex. No. | Atomic Ratio Mo:U | Heat-Treated Catalyst Temp. °F | Time, Hrs. | Reactor Temp. °F | Percent Conversion per Pass to Butadiene |
|---|---|---|---|---|---|
| 16 | 2/1 | 1050 | 3 | 800 | 43.2 |
| 17 | 3/1 | 1100 | 3 | 750 | 39.2 |

TABLE III-continued

| Ex. No. | Atomic Ratio Mo:U | Heat-Treated Catalyst Temp. °F | Time, Hrs. | Reactor Temp. °F | Percent Conversion per Pass to Butadiene |
|---|---|---|---|---|---|
| 18 | 8/1 | 1100 | 3 | 790 | 38.7 |

EXAMPLES 19-29

Promoted catalyst systems composed of molybdenum oxide, uranium oxide and at least one promoter element were prepared as described in Examples 3-6 and used for the oxidation of propylene to acrylonitrile. Catalysts with combinations of promoters, some of which are listed in the Table IV, were formulated by addition of that quantity of a soluble salt determined by the quantity of promoter desired in the catalyst, in a procedure similar to that described in Examples 3-6 hereinabove. A fixed bed microreactor was employed in the form of a 5/16-inch diameter tube, 5½ inches long, into which was charged about 7 g. of catalyst. The gas feed (propylene, ammonia and air) was metered by Rotameters. The Table IV below lists silica supported catalyst systems having various promoters used in runs at substantially atmospheric pressure with a feed molar ratio of Propylene/Ammonia/Air = 1/1.1/12 and an apparent contact time of about 3 seconds. In the formulae thought to define the active portions of the catalyst systems, the amount of oxygen is determined by that required to satisfy the average valences of the elements in the oxidation states in which they exist in the catalyst, and this amount is designated by the suffix $x$ for oxygen in the formulae.

TABLE IV

| Ex. No. | Catalyst | Heat-Treated Catalyst Temp. °F | Time, Hrs. | Reactor Temp. °F | Percent Conversion per Pass Acrylonitrile | Acetonitrile | HCN |
|---|---|---|---|---|---|---|---|
| 19 | $Mo_3U_3As_{0.25}O_x$ | 1075 | 3 | 820 | 61.7 | 2.3 | 4.6 |
| 20 | $Mo_3U_3Bi_{0.25}O_x$ | 1075 | 3 | 820 | 57.0 | 1.4 | 5.4 |
| 21 | $Mo_3U_3Sn_{0.25}O_x$ | 1075 | 3 | 820 | 26.8 | 3.2 | 1.5 |
| 22 | $Mo_3U_3V_{0.25}O_x$ | 1075 | 3 | 820 | 12.4 | 1.7 | 5.8 |
| 23 | $Mo_3U_3Fe_{0.25}O_x$ | 1075 | 3 | 820 | 9.4 | 2.8 | 8.0 |
| 24 | $Mo_3U_3Ni_6O_x$ | 1075 | 3 | 860 | 38.4 | 13.6 | Trace |
| 25 | $Mo_3U_3Co_6O_x$ | 1075 | 3 | 860 | 27.8 | 13.5 | 1.3 |
| 26 | $Fe_6BiU_6Mo_{12}O_x$ | 1075 | 3 | 860 | 48.0 | 6.7 | 4.6 |
| 27 | $Ni_6BiU_6Mo_{12}O_x$ | 1075 | 3 | 860 | 35.2 | 12.5 | Trace |
| 28 | $Fe_3Ni_3U_6Mo_{12}O_x$ | 1075 | 3 | 860 | 12.0 | 11.6 | 5.4 |
| 29 | $Fe_3Ni_3BiU_6Mo_{12}O_x$ | 1075 | 3 | 860 | 61.3 | 5.0 | 2.8 |

EXAMPLES 30-35

Promoted catalyst systems composed of molybdenum oxide, uranium oxide and at least one promoter element were prepared as described in Examples 19-29 and used for the oxidation of propylene to acrolein. A fixed bed microreactor was employed in the form of a 5/16-inch diameter tube, 5½ inches long, into which was charged about 7 g. of catalyst. The gas feed (propylene and air) was metered by Rotameters. The Table V below lists silica supported catalyst systems having various promoters used in runs at substantially atmospheric pressure with a feed molar ratio of Propylene/Air = 1/12 and an apparent contact time of about three seconds. In the formulae thought to define the active portions of the catalyst systems, the amount of oxygen is determined by that required to satisfy the average valences of the elements in the oxidation states in which they exist in the catalyst, and this amount is designated by the suffix $x$ for oxygen in the formulae.

TABLE V

| Ex. No. | Catalyst | Heat-Treated Catalyst Temp. °F | Time, Hrs. | Reactor Temp. °F | Percent Conversion per Pass Acrolein | Acrylic Acid |
|---|---|---|---|---|---|---|
| 30 | $Mo_3UAs_{0.25}O_x$ | 1075 | 3 | 840 | 53.4 | 3.2 |
| 31 | $Mo_3U_3As_{0.25}O_x$ | 1075 | 3 | 820 | 51.5 | 4.2 |
| 32 | $Mo_3U_3Bi_{0.25}O_x$ | 1075 | 3 | 820 | 50.2 | 5.3 |
| 33 | $Mo_3U_3Bi_{0.25}O_x$ | 1000 | 3 | 770 | 54.9 | — |
| 34 | $Mo_3U_3As_{0.25}O_x$ | 1000 | 3 | 770 | 56.8 | — |
| 35 | $Fe_3Ni_3BiU_6Mo_{12}O_x$ | 1075 | 3 | 810 | 57.8 | 6.9 |

EXAMPLES 36-38

Promoted catalyst systems composed of molybdenum oxide, uranium oxide and at least one promoter element were prepared as described in Examples 19-29 and used for the oxydehydrogenation of butylenes to butadiene. A fixed bed microreactor was employed in the form of a 5/16-inch diameter tube, 5½ inches long, into which was charged about 7 g. of catalyst. The gas feed in the examples below consisted of substantially pure 1-butene and air which was metered by Rotameters. Mixtures of butenes, or predominantly 2-butene, may also be used. The Table VI below lists silica supported catalyst systems having various promoters used in runs at substantially atmospheric pressure with a feed molar ratio of Butylenes/Air = 1/12 and an apparent contact time of about three seconds. In the formulae thought to define the active portion of the catalyst systems the amount of oxygen is determined by that required to satisfy the average valences of the elements in the oxidation states in which they exist in the catalyst, and this amount is designated by the suffix $x$ for oxygen in the formulae.

TABLE VI

| Ex. No. | Catalyst | Heat-Treated Catalyst Temp. °F | Time, Hrs. | Reactor Temp. °F | Percent Conversion per Pass to Butadiene |
|---|---|---|---|---|---|
| 36 | $MoUAs_{0.25}O_x$ | 1075 | 3 | 850 | 38.5 |
| 37 | $Mo_3U_3Bi_{0.25}O_x$ | 1075 | 3 | 820 | 43.7 |
| 38 | $Fe_3Ni_3BiU_6Mo_{12}O_x$ | 1075 | 3 | 800 | 57.2 |

We claim:

1. A catalyst composition consisting essentially of an activated catalytic oxide complex of uranium and molybdenum having a composition corresponding to the empirical chemical formula $U_xMo_yO_z$ where $x$ is a number within the range from 1 to about 25, $y$ is a number of from 1 to about 25, and $z$ is a number taken to satisfy the average valences of uranium and molybdenum in the oxidation states in which they exist in said catalyst.

2. The catalyst composition of claim 1 supported on a silica carrier.

3. A promoted catalyst composition consisting essentially of a base catalyst, a support and a promoter component, said base catalyst comprising the oxides of uranium and molybdenum, said support being silica and said promoter component comprising an oxide of at least one element selected from the group consisting of arsenic, bismuth, tin, vanadium, cobalt, nickel and iron, said catalyst composition corresponding to the empirical formula $M_aU_xMo_yO_z$ wherein M denotes at least one promoter element; $a$ is a number within the range of from about 0.001 up to about 3; $x$ is a number within the range of from 1 to about 25; and $y$ is a number of from 1 to about 25; and $z$ is a number taken to satisfy the average valences of uranium, molybdenum and the promoter element in the oxidation states in which they exist in the catalyst.

4. The promoted catalyst composition in accordance with claim 3, activated by heating at a temperature above 500°F but below a temperature deleterious to the catalyst.

5. The promoted catalyst composition, in accordance with claim 3, carried on a silica support comprising about 5 to about 95 percent by weight of said catalyst composition.

6. The catalyst composition in accordance with claim 1, activated by heating at a temperature above 500°F but below a temperature deleterious to the catalyst.

* * * * *